(12) United States Patent
Chen et al.

(10) Patent No.: US 11,497,855 B2
(45) Date of Patent: Nov. 15, 2022

(54) SMART DRUG INJECTION DEVICE

(71) Applicant: AMARILLO BIOSCIENCES, INC, Amarillo, TX (US)

(72) Inventors: Stephen T. Chen, Amarillo, TX (US); Hsien-Yao Chiu, New Taipei (TW)

(73) Assignee: AINOS, INC., San Diego, CA (US)

( * ) Notice: Subject to any disclaimer, the term of this patent is extended or adjusted under 35 U.S.C. 154(b) by 270 days.

(21) Appl. No.: 17/069,418

(22) Filed: Oct. 13, 2020

(65) Prior Publication Data
US 2021/0113777 A1  Apr. 22, 2021

(30) Foreign Application Priority Data
Oct. 18, 2019 (TW) ................. 108137797

(51) Int. Cl.
*A61M 5/315* (2006.01)
*A61M 5/34* (2006.01)
*A61M 5/31* (2006.01)

(52) U.S. Cl.
CPC ........ *A61M 5/31546* (2013.01); *A61M 5/344* (2013.01); *A61M 2005/3126* (2013.01); *A61M 2005/31588* (2013.01); *A61M 2205/18* (2013.01); *A61M 2205/35* (2013.01); *A61M 2205/502* (2013.01)

(58) Field of Classification Search
CPC .............. A61M 5/31546; A61M 5/344; A61M 2005/31588; A61M 2005/3126; A61M 2205/18; A61M 2205/35; A61M 2205/502
See application file for complete search history.

(56) References Cited

U.S. PATENT DOCUMENTS

| | | | |
|---|---|---|---|
| 2002/0013522 A1* | 1/2002 | Lav | A61B 5/150267 600/365 |
| 2015/0151048 A1* | 6/2015 | Okamoto | A61M 5/46 604/117 |
| 2015/0196707 A1* | 7/2015 | Moore | A61M 5/141 604/506 |

FOREIGN PATENT DOCUMENTS

CN  102406972 B  *  9/2012  ........ A61M 5/31546

OTHER PUBLICATIONS

Translation of CN102406972A (Year: 2019).*

* cited by examiner

*Primary Examiner* — Dung T Ulsh
(74) *Attorney, Agent, or Firm* — Rabin & Berdo, P.C.

(57) ABSTRACT

A smart drug injection device is disclosed, comprising a main body, a circuit board, a display, a syringe and a transmission mechanism; the main body comprises an accommodating space and a power button; the circuit board comprises a control unit and a storage unit; the transmission mechanism comprises a motor, a screw rod, a propelling block and a movable clamp, with the control unit electrically connected to the storage unit, the power button, the motor and the display, the motor connected to the screw rod, the propelling block movably arranged on the screw rod, the movable clamp disposed at one end of the propelling block and movable between two positions; the syringe is on one side of the main body and comprises a cylinder and a needle holder, one end of the cylinder has a needle and the other end is assembled with the needle holder.

8 Claims, 15 Drawing Sheets

SMART DRUG INJECTION DEVICE

CROSS-REFERENCE TO RELATED APPLICATION

This application claims the priority of Taiwanese patent application No. 108137797, filed on Oct. 18, 2019, which is incorporated herewith by reference.

BACKGROUND OF THE INVENTION

1. Field of the Invention

The present invention relates generally to a smart drug injection device, and more particularly, to a smart drug injection device able to automatically perform micro-injection at regular intervals and convenient to carry.

2. The Prior Arts

A drug injection device is a medical auxiliary device used to inject liquid drugs into the human body, and is often used in major hospitals and medical industries.

The general method to administer liquid drugs is either by oral or non-oral administration approach. The non-oral liquid drugs need to be injected into the human body through devices, such as syringes, by medical personnel so that the liquid drugs can be administered. Once the injection is completed, the syringe is discarded, which is convenient.

With the advancement of science and technology, medical technology has been continuously improved as well. Certain specific treatment methods require long-term drug injections to the patient, and the injection mode is often discontinuous, and needs to be performed at specific time intervals. Therefore, the patients not only have to wait for a long time, but medical staff must also stand by for a long time, so that the drug injection can be performed at specific time intervals.

However, when the hospital is understaffed, the nursing staff need to take care of multiple patients at the same time and thus cannot stand by one patient for a long time. Therefore, it often happens that the injection might be accidentally overlooked, which delays the treatment of the patient.

As a result, to save time in treatment, some hospitals and clinics will administer more dosages at one time; however, as time goes by, since the drugs will be absorbed by the body, the treatment result may not be as good as expected.

Furthermore, when the injection is performed by humans, the dosage of the drug may not be accurately measured, and the dosage is either too much or too little. For example, for patients with diabetes, if too much insulin is administered, the result could be either severe hypoglycemia, or may even put life in danger.

SUMMARY OF THE INVENTION

A primary objective of the present invention is to provide a smart drug injection device able to automatically perform injections to improve the understaff problem in the hospital so as to free the nursing staff from standing by the patient at any time, as well as to prevent the nursing staff from forgetting to inject and resulting in delay the treatment of the patient.

Another objective of the present invention is to provide a smart drug injection device, which is small in size and convenient to carry, so as to avoid the need for patients to wait in the hospital for a long time.

For achieving the foregoing objectives, the present invention provides a smart drug injection device, comprising a main body, a circuit board, a display, a syringe and a transmission mechanism.

The main body comprises an accommodating space and a power button, and the power button is arranged on the surface of the main body; the circuit board is disposed in the accommodating space and comprises a control unit and a storage unit. The control unit is electrically connected to the storage unit and the power button. The storage unit is used to store a weight value. The display is arranged on the surface of the main body and is electrically connected to the control unit, and the display is used to display the weight value and the injection dosage. The syringe is disposed on one side of the main body and comprises a cylinder and a needle holder, the cylinder is used to contain a drug, one end of the cylinder is disposed with a needle, the other end of the cylinder is used to assemble with the needle holder, the top of the needle holder is movably arranged in the cylinder. The transmission mechanism is disposed in the accommodating space, and comprises a motor, a screw rod, a propelling block and a movable clamp. The motor is electrically connected to the control unit. One output end of the motor is connected with the screw rod. The propelling block is movably disposed on the screw rod. The movable clamp is disposed at one end of the propelling block and can move between a first position and a second position relative to the propelling block. When the movable clamp is in the first position, the movable clamp clamps the bottom end of the needle holder on the propelling block. When the movable clamp is in the second position, the movable clamp loosens the bottom end of the needle holder to make the bottom end of the needle holder disengaged from the propelling block.

Wherein when the power button is pressed, the control unit controls the operation of the motor of the transmission mechanism, the motor drives the screw rod to rotate to make the propelling block move a specific distance, the propelling block drives the needle holder to move a specific distance relative to the cylinder, and the needle holder presses the liquid drug inside the cylinder to flow out from the needle, and the drug outflow is equal to the injection dosage.

In an embodiment of the present invention, the main body further comprises an up button, a down button, a confirm button, and a stop button; the up button, the down button, the confirm button and the stop button are arranged on the surface of the main body and are electrically connected to the control unit; when the up button is pressed, the weight value in the storage unit is increased; when the down button is pressed, the weight value in the storage unit is decreased; when the confirm button is pressed, the storage unit sends the weight value to the control unit; when the stop button is pressed, the control unit stops the motor operation.

Wherein the circuit board further comprises a timing unit, electrically connected to the control unit; when the confirm button is pressed, the timing unit starts to count down from a predetermined time value, and sends a time message to the control unit for every interval of time, so that the control unit controls the motor to drive the screw rod to rotate to move the propelling block; when the countdown is completed, an alarm is issued to remind the medical staff; wherein the display is used to display the predetermined time value.

In an embodiment of the present invention, the smart drug injection device further comprises at least one positioning sleeve, which is disposed on one side of the main body, and the propelling block is protrudingly disposed on the same side of the main body where the positioning sleeve is disposed, and the positioning sleeve is used for fastening the cylinder.

In an embodiment of the present invention, the main body further comprises a positioning hole opened on one side of the main body and located between the positioning sleeve and the propelling block, and the cylinder comprises a wing portion inserted into the positioning hole.

In an embodiment of the present invention, the smart drug injection device further comprises a protective cover, the protective cover has a hole, the hole is opened at one end of the protective cover, the protective cover is detachably disposed on one side of the main body, the syringe is disposed inside the protective cover, and the hole is used for the cylinder to pass through.

In an embodiment of the present invention, the propelling block further comprises at least two latch holes, the movable clamp further comprises a latch block and an elastic piece, the latch block is disposed on the elastic piece, and the latch block can be selectively disposed in one of the at least two latch holes.

In an embodiment of the present invention, the propelling block further comprises a positioning clamp, the positioning clamp comprises two clamp bodies and an elastic element, the two clamp bodies are pivotally connected to each other, and the two ends of the clamp bodies respectively have a first clamping opening and a second clamping opening, the elastic element is disposed on the first clamping opening, two ends of the elastic element are respectively connected with the clamping bodies, and the second clamping opening is clamped on the screw rod.

In an embodiment of the present invention, the syringe further comprises a delivery tube and a sheath clamp, one end of the delivery tube is connected to the needle, the sheath clamp comprises a channel, the channel has a large-diameter end and a small-diameter end, the inner diameter of the large-diameter end is greater than the outer diameter of the delivery tube, the inner diameter of the small-diameter end is smaller than the outer diameter of the delivery tube, and the delivery tube is movably disposed in the channel.

The effect of the present invention is that after the user inputs the patient information to the storage unit, the control unit controls the transmission mechanism so that the syringe can perform injection automatically, and the understaff problem in the hospital is improved, and the nursing staff does not need to stand by the patient all the time, as well as to prevent the nursing staff from accidentally forgetting the injection due to busyness and delaying the patient's treatment. At the same time, the treatment and results are recorded so as to provide medical staff for reference and observation.

Furthermore, the timing unit and the control unit enable the syringe to automatically perform microinjections at regular intervals, avoiding the situation where the dosage of the drug is not accurate, and avoiding excessive dosage by hospitals and clinics to save time, leading to poor result of treatment.

In addition, the present invention is simple in structure, small in size and convenient to carry, which eliminates the need for patients to wait in the hospital for a long time.

Wherein, the control unit of the present invention follow a plan for the patient made by the physician, then store the treatment course, result, time and personal data in the storage unit, and display the corresponding information status, pattern and provision of light source at night under the setting through the display, which is convenient for medical staff to observe; wherein, the information and patterns can be battery capacity, physiological model calculation of injection dosage and concentration, injection in progress, total dosage and warnings.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention.

Figure 1:
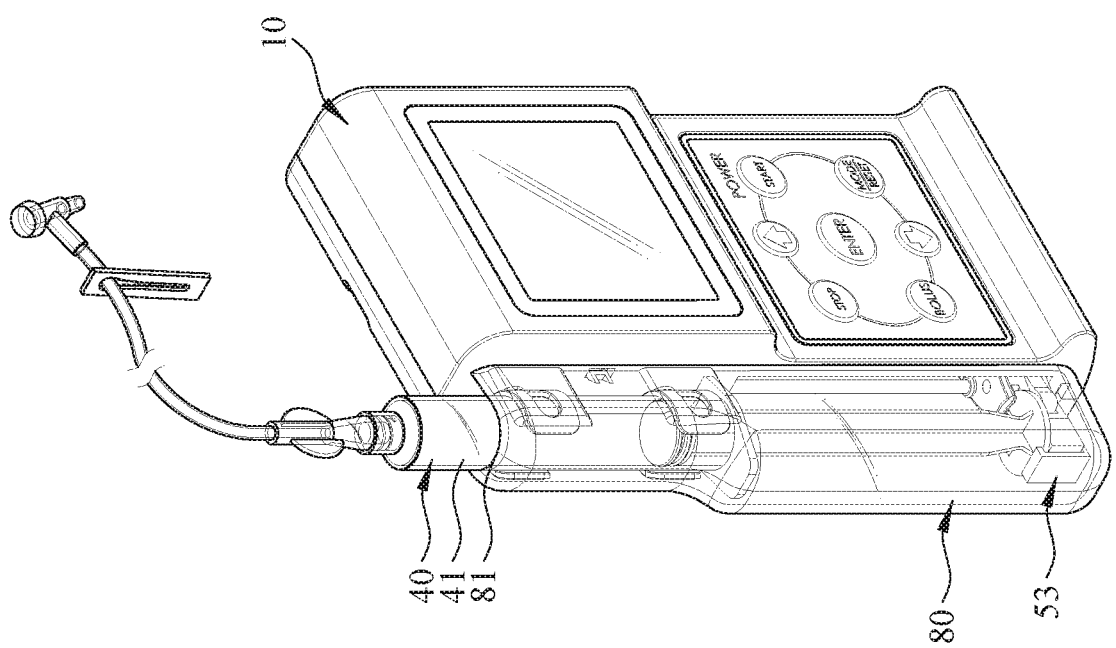
FIG. 1 is a perspective view of a smart drug injection device according to a preferred embodiment of the present invention.
Figure 2:
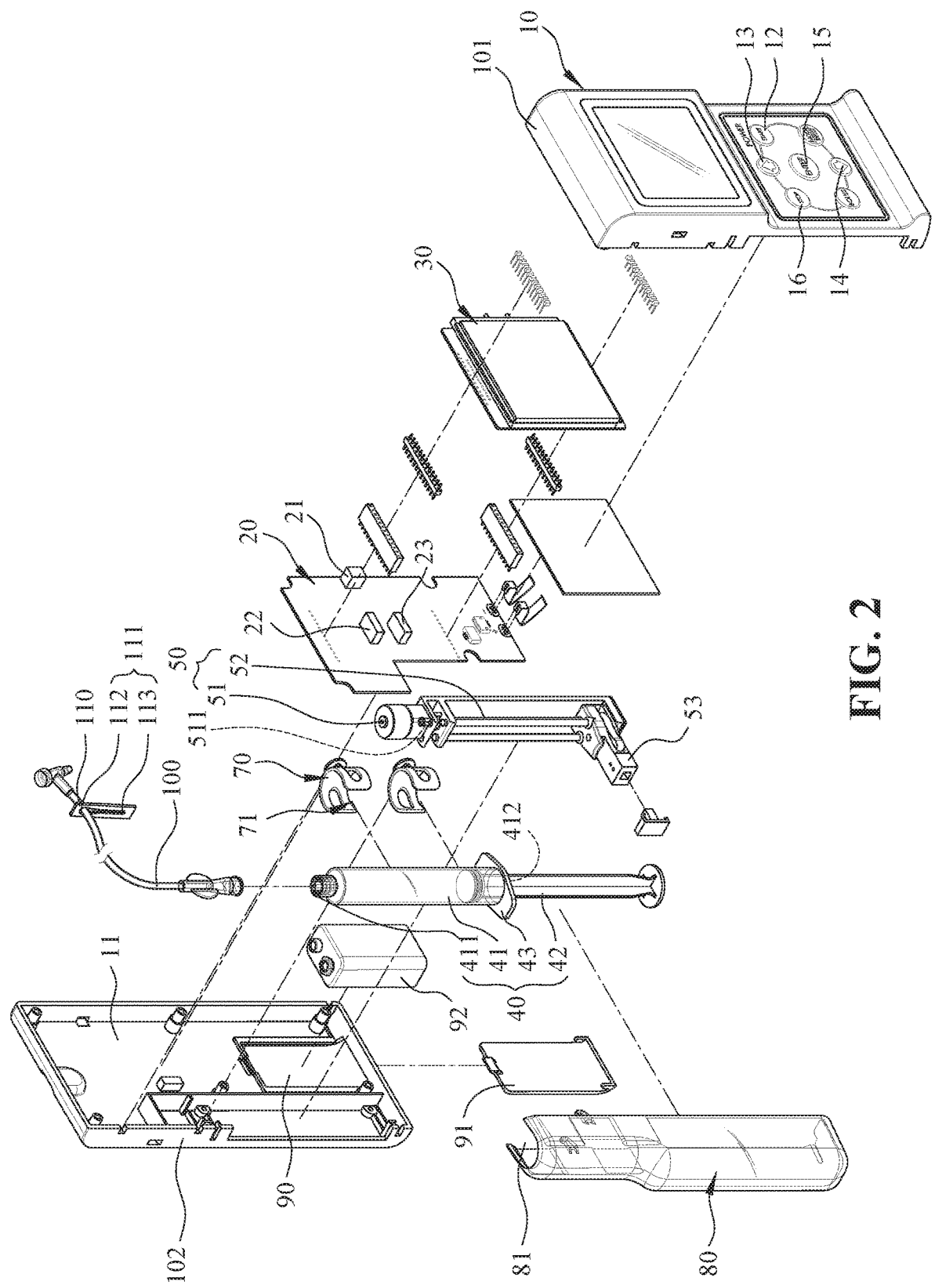
FIG. 2 is a perspective exploded view of the smart drug injection device of a preferred embodiment of the present invention.
Figure 3:
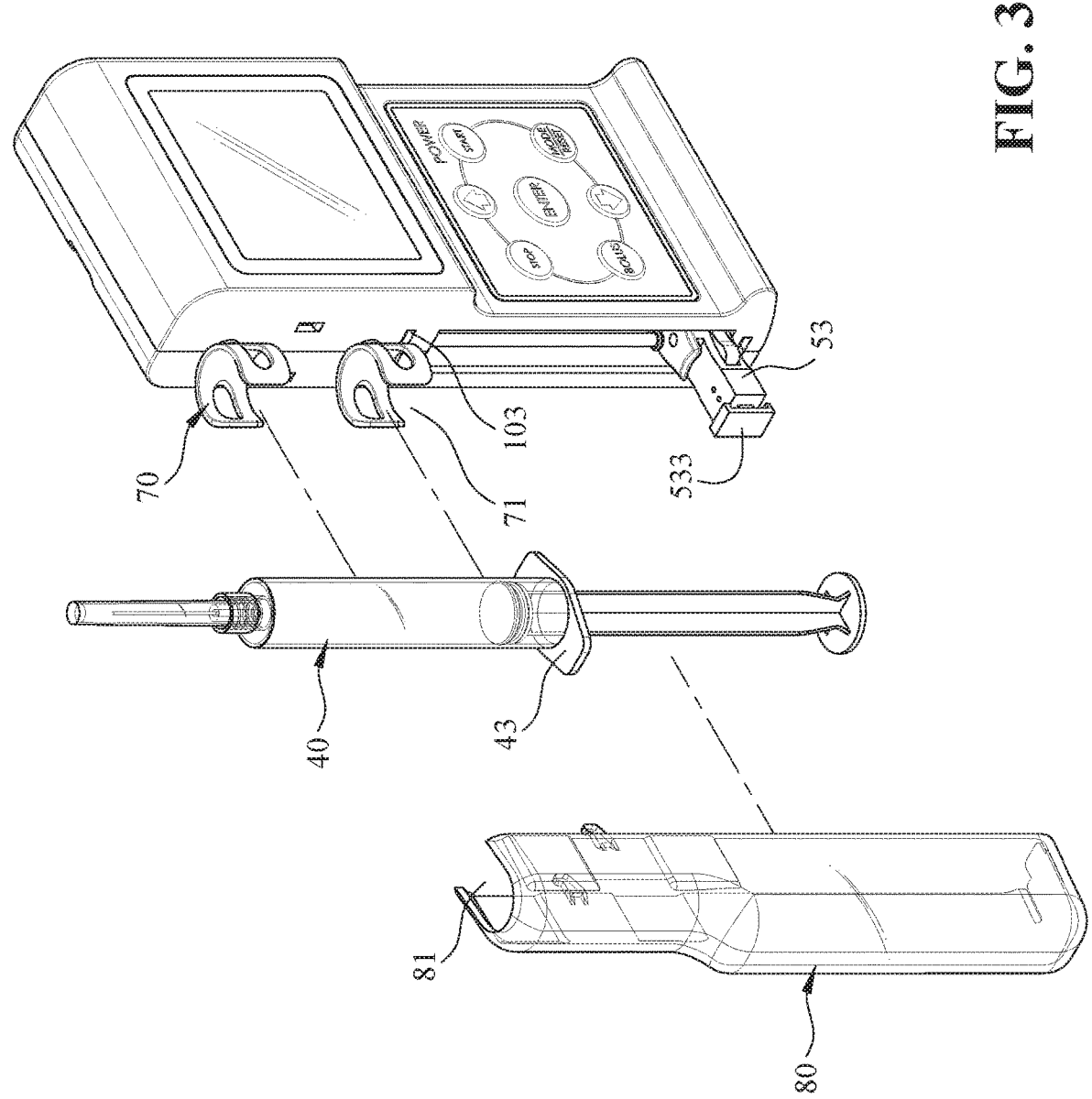
FIG. 3 is another perspective exploded view of the smart drug injection device of a preferred embodiment of the present invention.

Referring to FIG. 1, FIG. 2 and FIG. 3, FIG. 1 is a perspective view of a smart drug injection device according to a preferred embodiment of the present invention; FIG. 2 is a perspective exploded view of the smart drug injection device of a preferred embodiment of the present invention; FIG. 3 is another perspective exploded view of the smart drug injection device of a preferred embodiment of the present invention. As shown in FIGS. 1-3, the present invention provides a smart drug injection device, comprising: a main body 10, a circuit board 20, a display 30, a syringe 40, and a transmission mechanism 50.

The main body 10 comprises an accommodating space 11 and a power button 12, and the power button 12 is arranged on the surface of the main body 10. Specifically, in a preferred embodiment of the present invention, the main body 10 comprises a first shell 101 and a second shell 102, forming a main body 10 with the accommodating space 11. The power button is disposed on the surface of the first shell 101.

The circuit board 20 is disposed in the accommodating space 11 and comprises a control unit 21 and a storage unit 22. The control unit 21 is electrically connected to the storage unit 22 and the power button 12. The storage unit 22 is used to store a weight value (not shown). The control unit 21 calculates an injection dosage (not shown) according to the weight value.

The display 30 is disposed on the surface of the main body 10 and is electrically connected to the control unit 21, and the display 30 is used to display the weight value and the injection dosage. Specifically, in a preferred embodiment of the present invention, the display 30 is disposed on the first shell 101.

The syringe 40 is disposed on one side of the main body 10 and comprises a cylinder 41 and a needle holder 42, one end of the cylinder 41 is disposed with a needle 411, the other end of the cylinder 41 has an opening 412. The cylinder 41 is for containing a drug 44 (refer to FIG. 7). The opening 412 at the end of the cylinder 41 is used to assemble with the needle holder 42, and the top of the needle holder 42 is movably arranged in the cylinder 41. Specifically, the drug 44 enters the cylinder 41 through the opening 412. A top end of the needle holder 42 is disposed in the cylinder 41 through the opening 412, and can move in the cylinder 41; when the top of the needle holder 42 moves towards the end with the needle 411, the air and the drug 44 inside the cylinder 41 will be squeezed to make the air or drug 44 flow out of the needle 411; on the other hand, when the top end of the needle holder 42 moves toward the opposite direction of the end of the cylinder 41 with the needle 411, the air or drug 44 will be drawn into the cylinder 41 from the needle 411.

The transmission mechanism 50 is disposed in the accommodating space 11, and comprises a motor 51, a screw rod 52, a propelling block 53 and a movable clamp 533. The motor 51 is electrically connected to the control unit 21. One output end 511 of the motor 51 is connected with the screw rod 52. The propelling block 53 is movably disposed on the screw rod 52.

Figure 4:
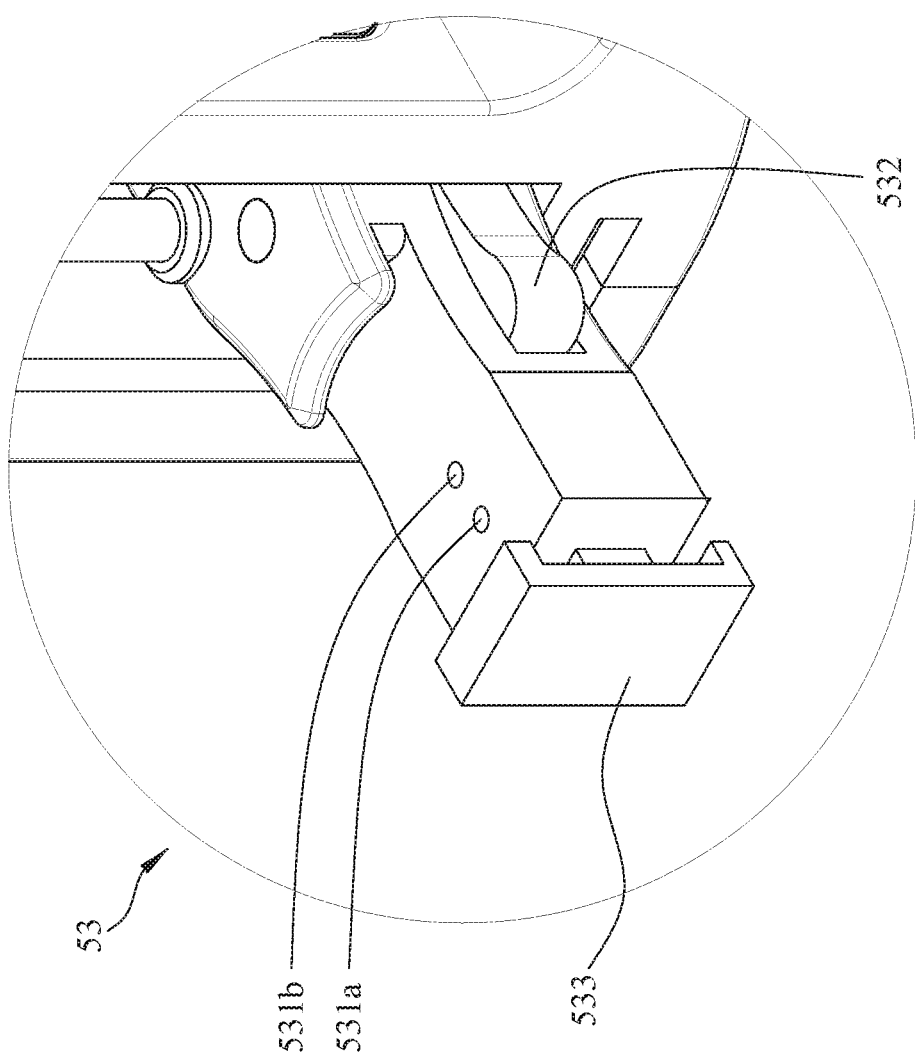
FIG. 4 is a partial enlarged view of the propelling block of the smart drug injection device of a preferred embodiment of the present invention.
Figure 5:
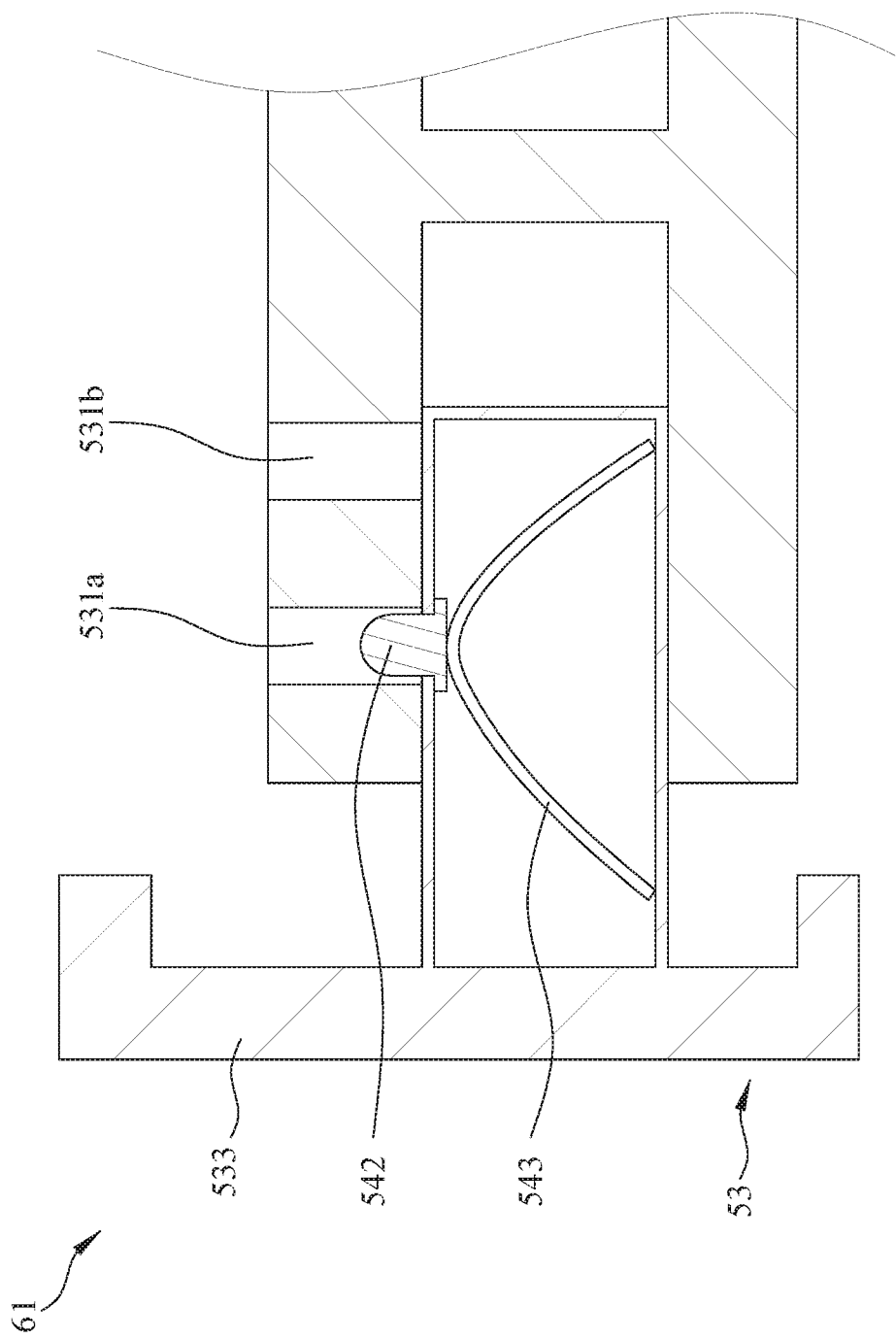
FIGS. 5, 6 and 7 are respectively schematic cross-sectional views of the actions of the movable clamp of the smart drug injection device of the preferred embodiment of the present invention clamping the bottom end of the needle holder on the propelling block.
Figure 6:
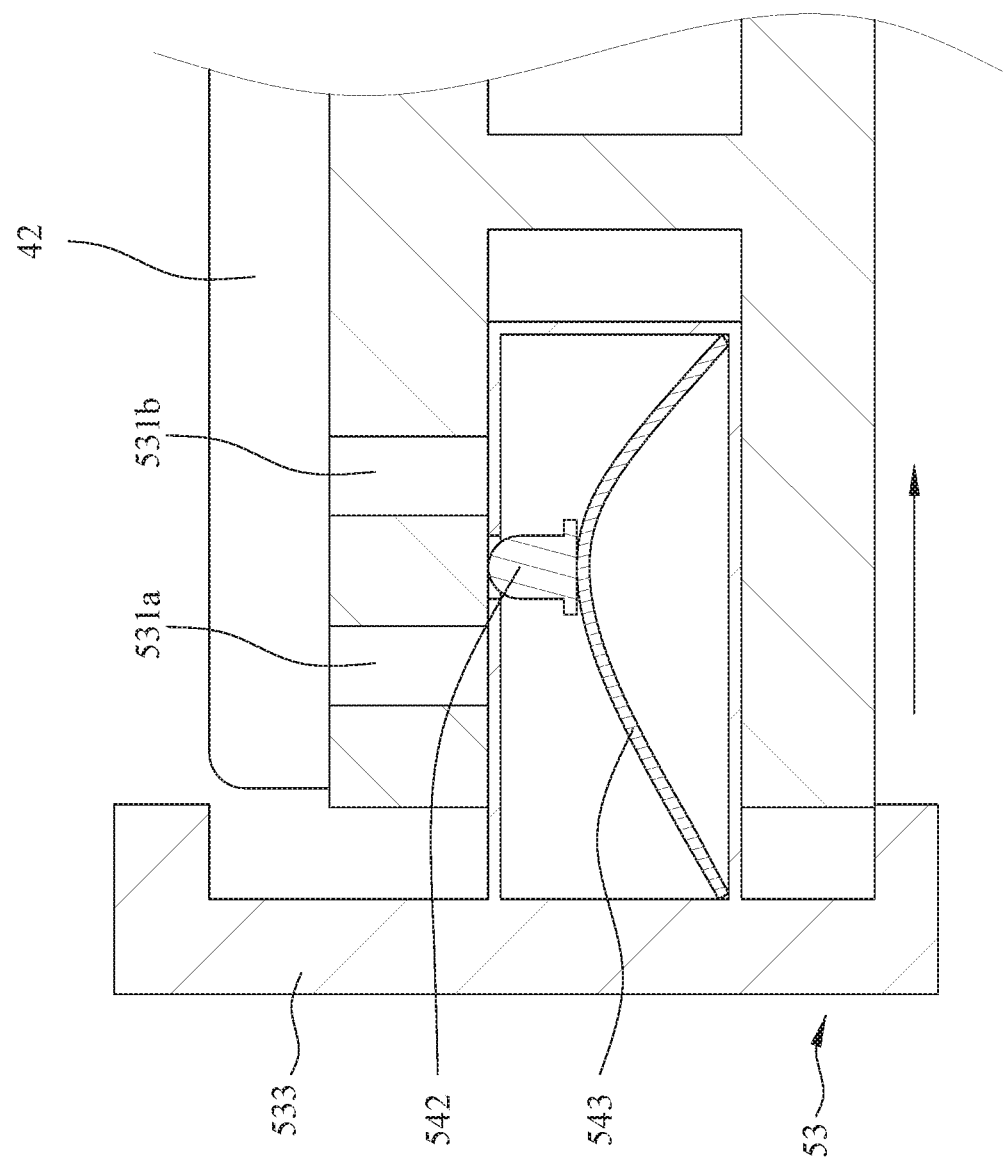
Figure 7:
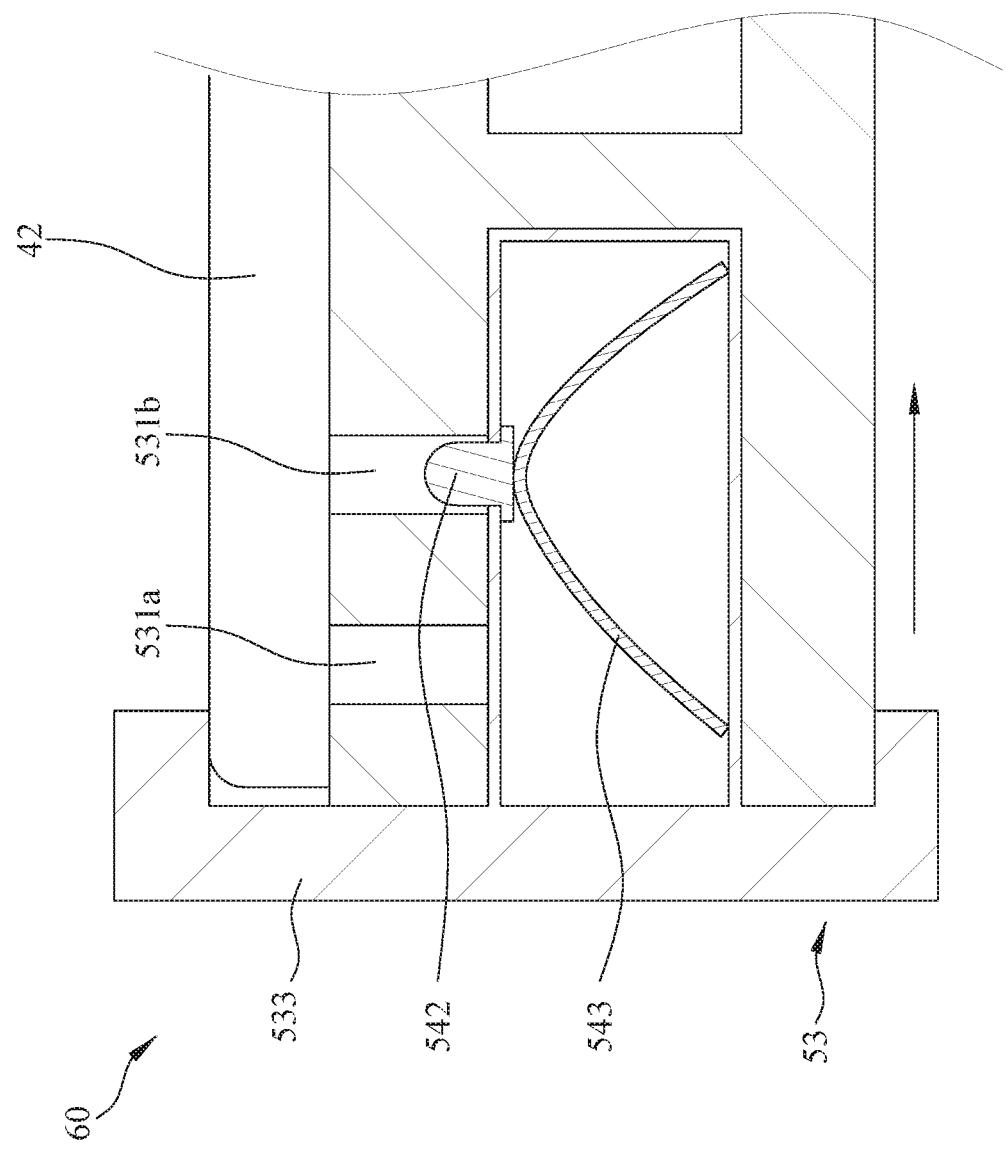
Figure 8:
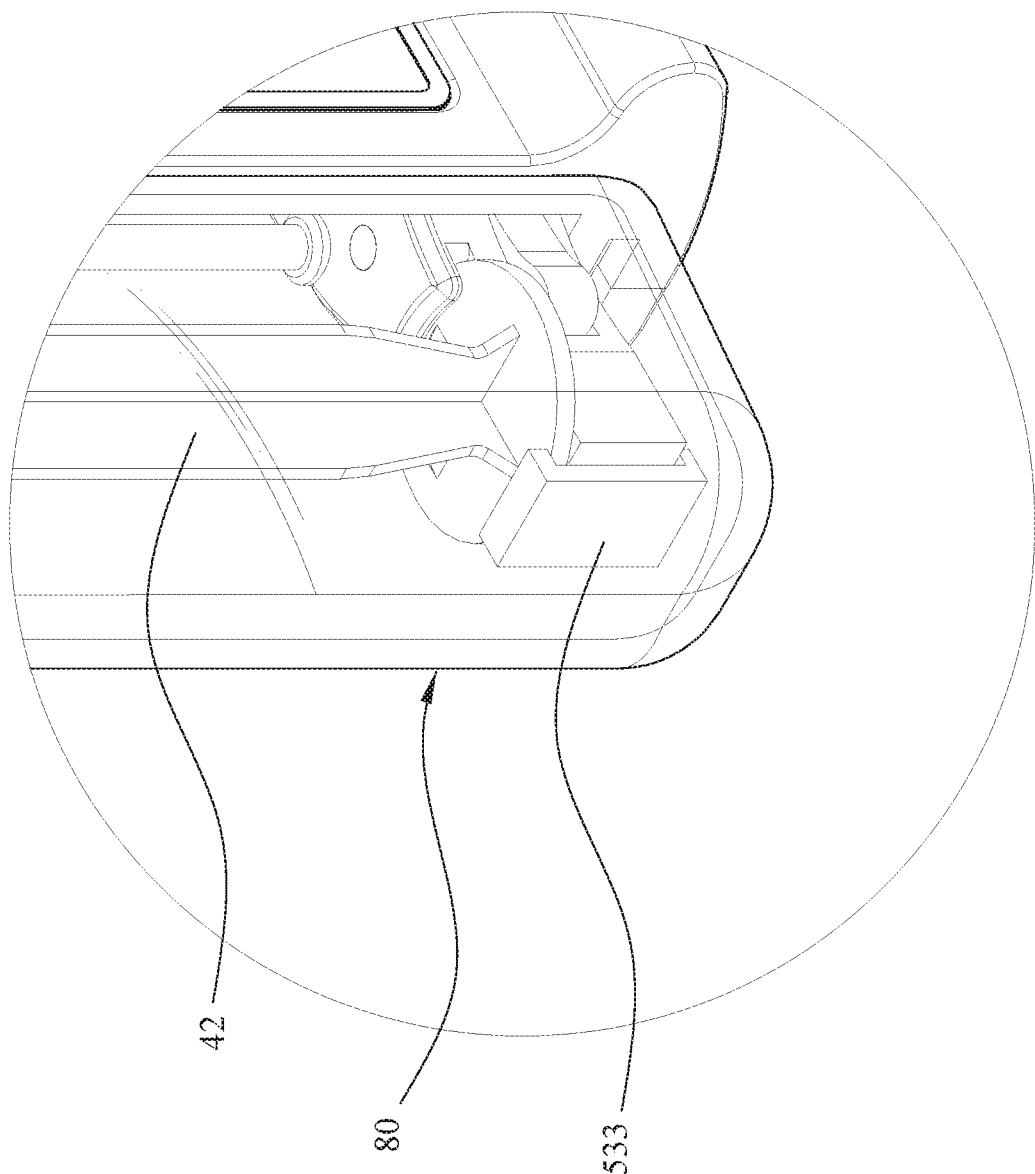
FIG. 8 is a schematic view of assembling the propelling block, movable clamp and needle holder of the smart drug injection device of the preferred embodiment of the present invention.

FIG. 4 is a partial enlarged view of the propelling block of the smart drug injection device of a preferred embodiment of the present invention; FIGS. 5, 6 and 7 are respectively schematic cross-sectional views of the actions of the movable clamp of the smart drug injection device of the preferred embodiment of the present invention clamping the bottom end of the needle holder on the propelling block; FIG. 8 is a schematic view of assembling the propelling block, movable clamp and needle holder of the smart drug injection device of the preferred embodiment of the present invention. As shown in FIGS. 4-8, in a preferred embodiment of the present invention, the movable clamp 533 is disposed at one end of the propelling block 53 and can move between a first position 60 and a second position 61 relative to the propelling block 53. When the movable clamp 533 is at the second position 61, the bottom end of the needle holder 42 can be placed on the propelling block 53; when the movable clamp 533 is at the first position 60, the movable clamp 533 clamps the bottom end of the needle holder 42 on the propelling block 53, which completes the mounting of the needle holder 42. when the injection is completed and the syringe 40 needs to be removed, the movable clamp 533 can be moved to the second position 61 again, so that the movable clamp 533 loosens the clamping on the bottom end of the needle holder 42, and the bottom end of the needle holder 42 can be separated from the propelling block 53.

Specifically, in a preferred embodiment of the present invention, the propelling block 53 further comprises at least two latch holes 531a, 531b, the movable clamp 533 further comprises a latch block 542 and an elastic piece 543, the latch block 542 is disposed on the elastic piece 543, and the latch block 542 can be selectively disposed in one of the at least two latch holes 531a, 531b, so that the propelling block 53 is moved between the first position 60 and the second position 61. Thereby, the movable clamp 533 can perform quick fixation of the bottom end of the needle holder 42 onto the propelling block 53.

As shown in FIG. 5, when the movable clamp 533 is at the second position 61, the movable clamp 533 is far away from the propelling block 53, and the latch block 542 of the movable clamp 533 is disposed in the latch hole 531a; at this point, the user can put the bottom end of the needle holder 42 on the propelling block 53.

As shown in FIG. 6, after the bottom end of the needle holder 42 is set on the propelling block 53, the user can move the movable clamp 533 in the direction of the propelling block 53. At this point, the latch block 542 is pressed to move downwards and will squeeze the elastic piece 543 below; when the user continues to move the movable clamp 533 in the direction of the propelling block 53 to the first position 60, the latch block 542 of the movable clamp 533 is bounced by the force of the elastic piece 543 to set in the latch hole 531b to achieve positioning the movable clamp 533.

As shown in FIG. 7, when the movable clamp 533 moves to the first position 60, the movable clamp 533 clamps the bottom end of the needle holder 42a onto the propelling block 53, to achieve t fixing the bottom end of the needle holder 42a. When the injection is completed and the syringe 40 needs to be removed, the movable clamp 533 can be moved to the second position 61 again, so that the movable clamp 533 loosens the clamping on the bottom end of the needle holder 42 and the bottom end of the needle holder 42 can be separated from the propelling block 53.

As shown in FIG. 3, in an embodiment of the present invention, the smart drug injection device further comprises at least one positioning sleeve 70, and the main body 10 further comprises a positioning hole 103; the at least one positioning sleeve 70 is disposed on one side of the main body 10, and the propelling block 53 is protrudingly disposed on the same side of the main body 10; the positioning sleeve 70 is for fastening the cylinder 41. In a preferred embodiment, the at least one positioning sleeve 70 includes a sleeve opening 71. The inner diameter of the positioning sleeve 70 is greater than the outer diameter of the cylinder 41, so that the positioning sleeve 70 can be sleeved on the cylinder 41. When assembling the syringe 40, the cylinder 41 can be quickly fixed in the positioning sleeve 70 through the sleeve opening 71; and when the syringe 40 needs to be disassembled, the cylinder 41 can be directly taken out of the sleeve opening 71 of the positioning sleeve 70 to achieve rapid assembly and disassembly. Preferably, in the preferred embodiment of the present invention, there are two positioning sleeves 70 on one side of the main body 10; however, the number of positioning sleeves 70 is not limited to any specifics. In order to make the syringe 40 sturdier, more positioning sleeve 70 can be added.

The positioning hole 103 is opened on one side of the main body 10 and located between the positioning sleeve 70 and the propelling block 53, and the cylinder 41 comprises a wing portion 43 inserted into the positioning hole 103. Through the insertion of the wing portion 43 in the positioning hole 103, the fixation of the syringe 40 can be sturdier.

As such, when the control unit 21 controls the motor 51 to drive the screw rod 52 to rotate to move the propelling block 53 and the propelling block 53 pushes the bottom end of the needle holder 42, the cylinder 41 of the syringe 40 will not move thereby, thus, achieve the function of positioning the cylinder 41.

In an embodiment of the present invention, the smart drug injection device further comprises a protective cover 80, the protective cover 80 has a hole 81, the hole 81 is opened at one end of the protective cover 80, the protective cover 80 is detachably disposed on one side of the main body 10, the syringe 40 is disposed inside the protective cover 80, and the hole 81 is used for the cylinder 41 to pass through. Preferably, in the preferred embodiment of the present invention, the protective cover 80 is a transparent cover, so that the user can check the remaining amount of the drug 44 (shown in FIG. 10) in the syringe 40 through the protective cover 80.

Figure 9:
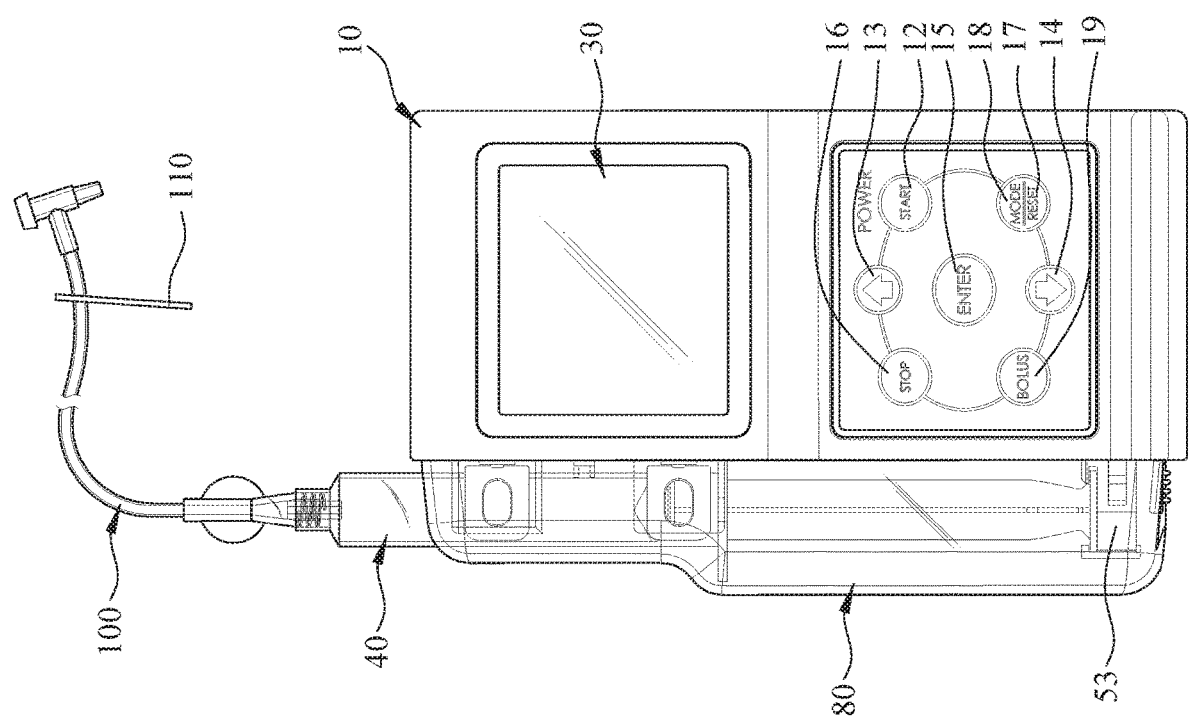
FIG. 9 is a front view of the smart drug injection device of the preferred embodiment of the present invention.

FIG. 9 is a front view of the smart drug injection device of the preferred embodiment of the present invention. As shown in FIG. 9, in a preferred embodiment of the present invention, the main body 10 further comprises an up button 13, a down button 14, a confirm button 15, and a stop button 16; the up button 13, the down button 14, the confirm button 15 and the stop button 16 are arranged on the surface of the first shell 101 of the main body 10 and are electrically connected to the control unit 21; when the up button 13 is pressed, the weight value in the storage unit 22 is increased; when the down button 14 is pressed, the weight value in the storage unit 22 is decreased; when the confirm button 15 is pressed, the storage unit 22 sends the weight value to the control unit 21; when the stop button 16 is pressed, the control unit 21 stops the operation of the motor 51.

Wherein, the circuit board 20 further comprises a timing unit 23, electrically connected to the control unit 21; when the confirm button 15 is pressed, the timing unit 23 starts to count down from a predetermined time value (not shown), and sends a time message to the control unit 21 for every interval of time, so that the control unit 21 controls the motor 51 to drive the screw rod 52 to rotate to move the propelling block 53; wherein the display 30 is used to display the predetermined time value (not shown).

Figure 10:
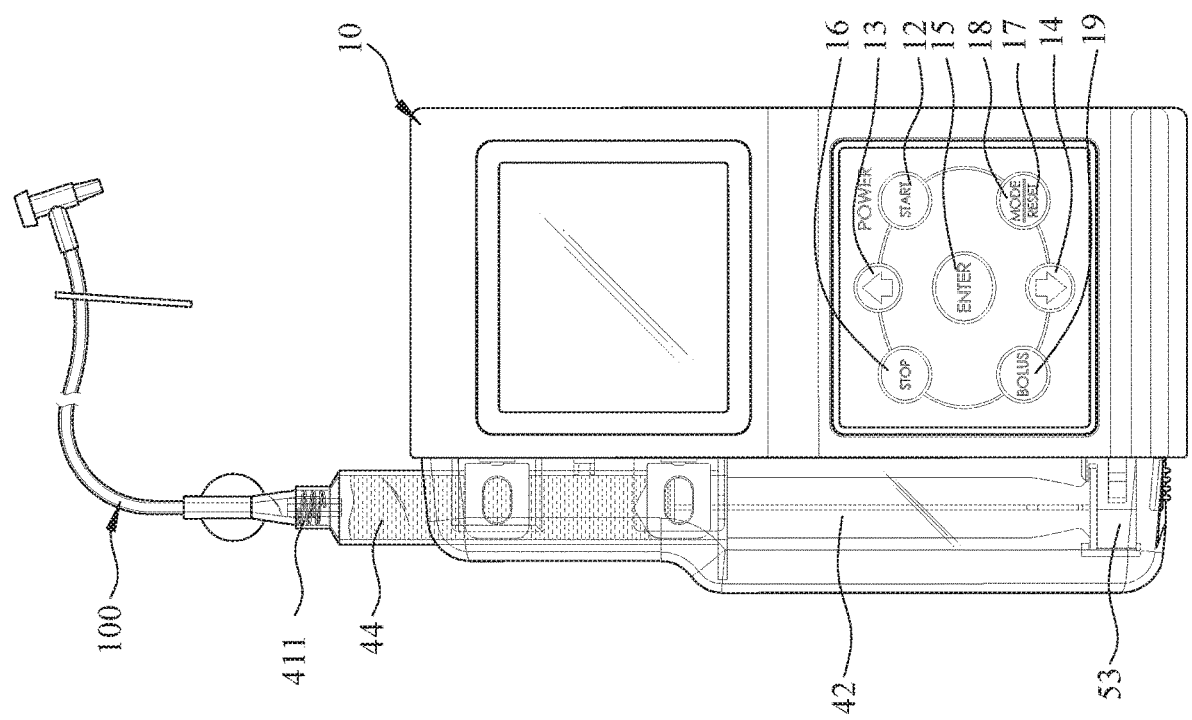
FIGS. 10 and 11 are schematic views of the actions of the smart drug injection device according to the preferred embodiment of the present invention injecting drug.
Figure 11:
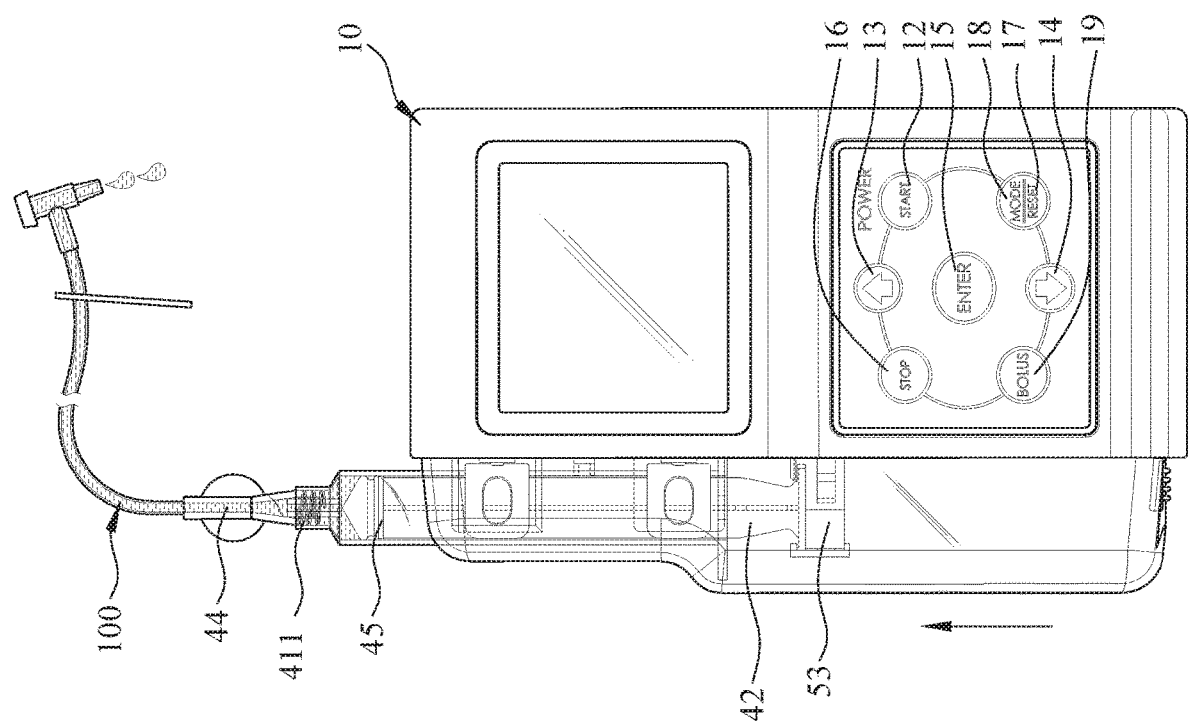
Figure 12:
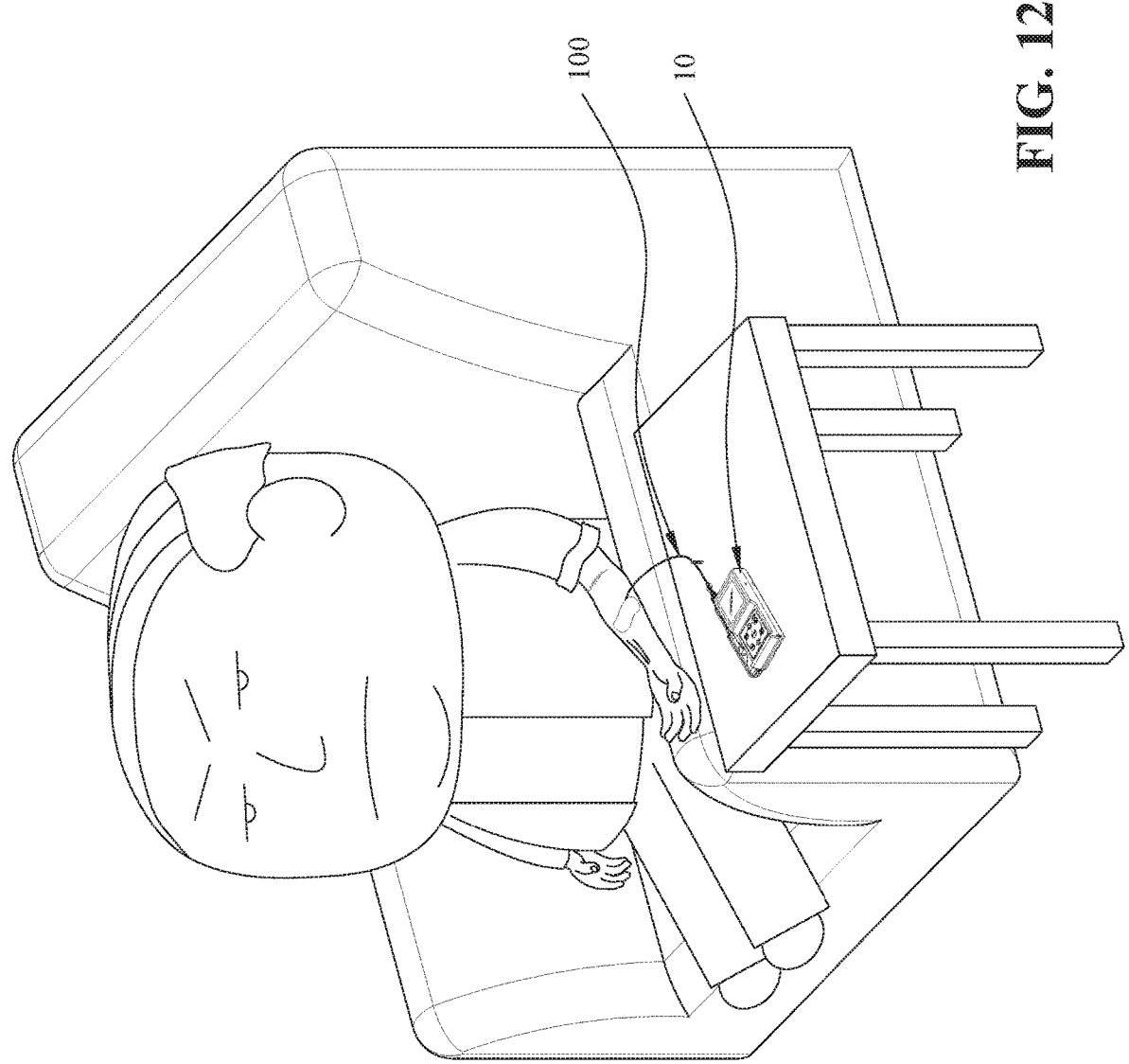
FIG. 12 is a schematic view of a first use mode of the smart drug injection device according to the preferred embodiment of the present invention.

FIGS. 10 and 11 are schematic views of the actions of the smart drug injection device according to the preferred embodiment of the present invention injecting drug. As shown in FIGS. 11-12, when the power button 12 is pressed, the storage unit 22 sends the weight value to the control unit 21, and the control unit 21 controls the operation of the motor 51 of the transmission mechanism 50, the motor 51 drives the screw rod 52 to rotate to make the propelling block 53 move a specific distance, the propelling block 53 drives the needle holder 42 to move a specific distance relative to the cylinder 41, and the needle holder 42 presses the drug 44 inside the cylinder 41 to flow out from the needle 411, and the drug outflow is equal to the injection dosage.

Preferably, the main body 10 further includes a mode button 18, a reset button 17, and an injection button 19. The mode button 18, the reset button 17, and the injection button 19 are disposed on the surface of the first shell 101 of the main body 10, and are electrically connected to the control unit 21.

When using the present invention for the first time, the user can first press the mode button 18 three times to input the patient's weight, and adjust the weight value by the up button 13 and the down button 14; when the desired weight value is reached, the user then presses the confirm button 15 to input; the display 30 will display the concentration value that needs to be administered to the patient, the user presses the confirm button 15 again to input; the display 30 will display the dosage range setting (for example, 10 u/ml-50 u/ml, per unit 0.01 ml), the user can adjust the required injection dosage with the up button 13 and down button 14. After the adjustment is completed, the confirm button 15 is pressed to confirm; finally, the display 30 displays the injection time and the total number of pulses, and press the confirm button 15 to input to complete the patient's weight data input. In a preferred embodiment of the present invention, the minimum dosage is 10 u/ml.

When the air in the syringe 40 needs to be expelled, press the mode button 18 twice, followed by a long press on the confirm button 15 to confirm, the display 30 will display an air-expelling state, and the control unit 21 will control the motor 51 of the transmission mechanism 50 to operate. The motor 51 drives the screw rod 52 to rotate to move the propelling block 53, and the propelling block 53 drives the needle holder 42 to move relative to the cylinder 41. The needle holder 42 will squeeze the air in the cylinder 41 to flow out from the needle 411. After the air is exhausted, the user can release the confirm button 15 and the control unit 21 stops the motor 51 of the transmission mechanism 50.

After the air in the syringe 40 is expelled, the patient can be injected with drug. By pressing the power button 12, the confirm button 15 and the injection button 19 in sequence, the smart drug injection device will start the first delivery of the drug 44. In a preferred embodiment of the present invention, the smart drug injection device will perform five drug injections, and each time interval is six minutes, wherein after starting the injection, the user can reset the dosage to zero at any time by pressing the reset button 17.

In a preferred embodiment of the present invention, the circuit board 20 further includes a player (not shown). The player is electrically connected to the control unit 21. Each time the injection is started, the player will issue a warning sound to remind the users that the smart drug injection device has started an injection task. When the injection task is finished, the player will issue a warning sound to remind the user that the smart drug injection device has finished the injection task.

Furthermore, during the injection by the smart drug injection device, the display 30 will be turned off to enter a black screen, i.e., power-saving, state; if the user wants to view the information on the display 30 during the injection, the user can press the injection button 19 to awake display 30. In addition, during the injection, the user can press the mode button 18 to awake the display 30 to display the dosage already injected.

When the dosage needs to be changed, the injection can be paused by pressing the stop button 16 and the confirm button 15. The user can re-enter the patient's weight data by pressing the mode button 18 three times. After the data is entered, the user can press the stop button 16 to end the setting; then press the power button 12, confirm button 15 and injection button 19 in sequence to continue the previous injection course.

After the injection is completed, the user can return the display 30 to the standby screen by pressing the stop button 16.

In a preferred embodiment of the present invention, the syringe 40 further comprises a delivery tube 100 and a sheath clamp 110, one end of the delivery tube 100 is connected to the needle 411 of the syringe 40, the sheath clamp 110 comprises a channel 111, the channel 111 has a large-diameter end 112 and a small-diameter end 113, the inner diameter of the large-diameter end 112 is greater than the outer diameter of the delivery tube 100, the inner diameter of the small-diameter end 113 is smaller than the outer diameter of the delivery tube 100, and the delivery tube 100 is movably disposed in the channel 111.

During injecting the drug 44, the delivery tube 100 is moved to the large-diameter end 112 in the channel 111 so that the drug 44 can be transported to the other end through the delivery tube 100; when the injection of the drug 44 needs to be suspended or stopped, the delivery tube 100 is moved to the small-diameter end 113 in the channel 111. Since the inner diameter of the small-diameter end 113 is smaller than the outer diameter of the delivery tube 100, when the delivery tube 100 moves to the small-diameter end 113 in the channel 111, the small-diameter end 113 will squeeze the delivery tube 100 so that the drug 44 cannot pass through the delivery tube 100, which avoids the situation that the drug 44 in the delivery tube 100 still flows out of the delivery tube 100 when the administration of the drug 44 is suspended, resulting in unnecessary waste.

FIG. 12 is a schematic view of a first use mode of the smart drug injection device according to the preferred embodiment of the present invention. As shown in FIG. 12, when in use, the smart drug injection device of the present invention can be placed on the desktop, and the user can press the power button 12 to inject the drug 44.

Figure 13:
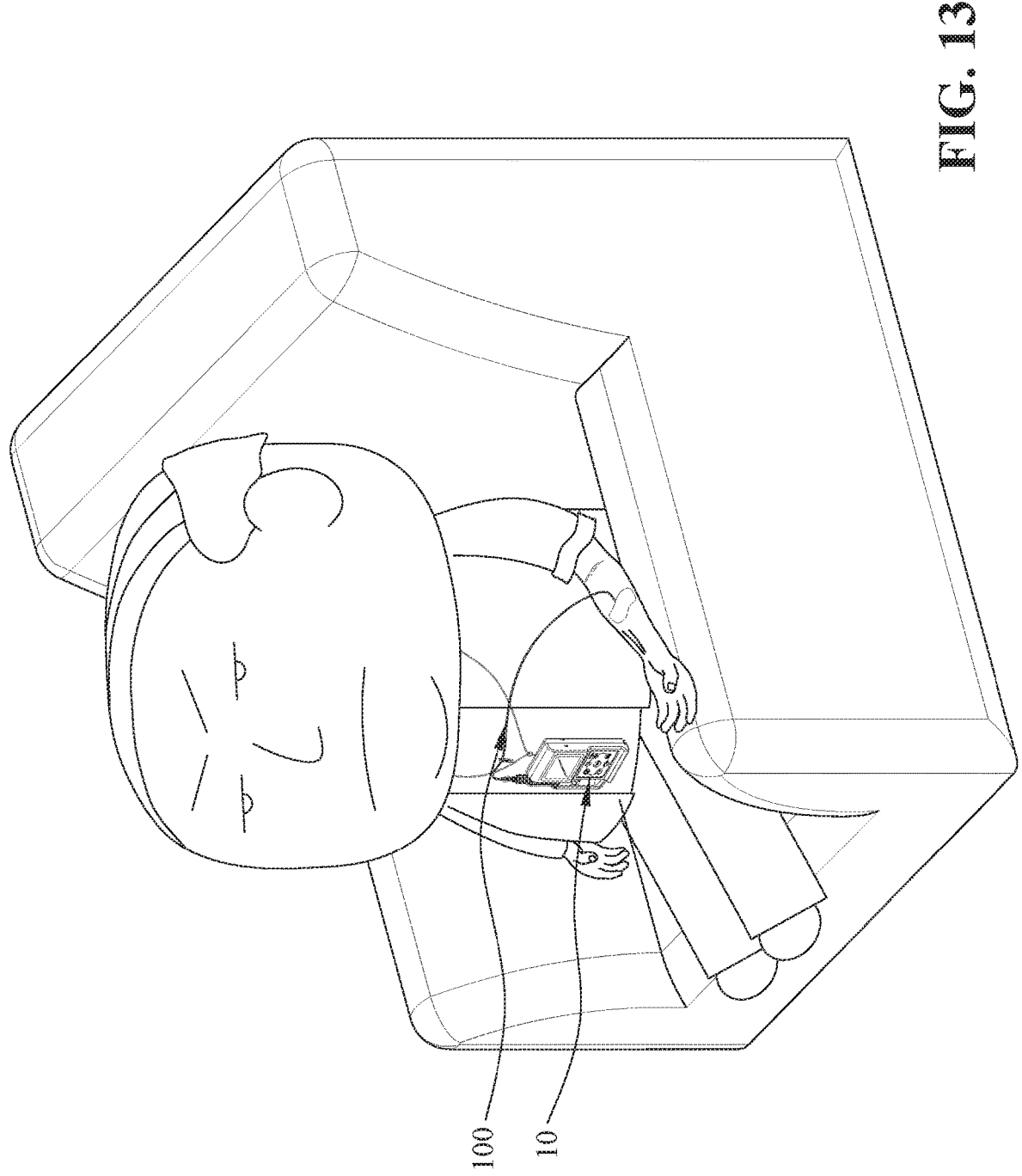
FIG. 13 is a schematic view of a second use mode of the smart drug injection device according to the preferred embodiment of the present invention.

FIG. 13 is a schematic view of a second use mode of the smart drug injection device according to the preferred embodiment of the present invention. As shown in FIG. 13, the smart drug injection device of the present invention can be further hung on the neck of the user to facilitate the user to carry around and to inject the drug 44.

Figure 14:
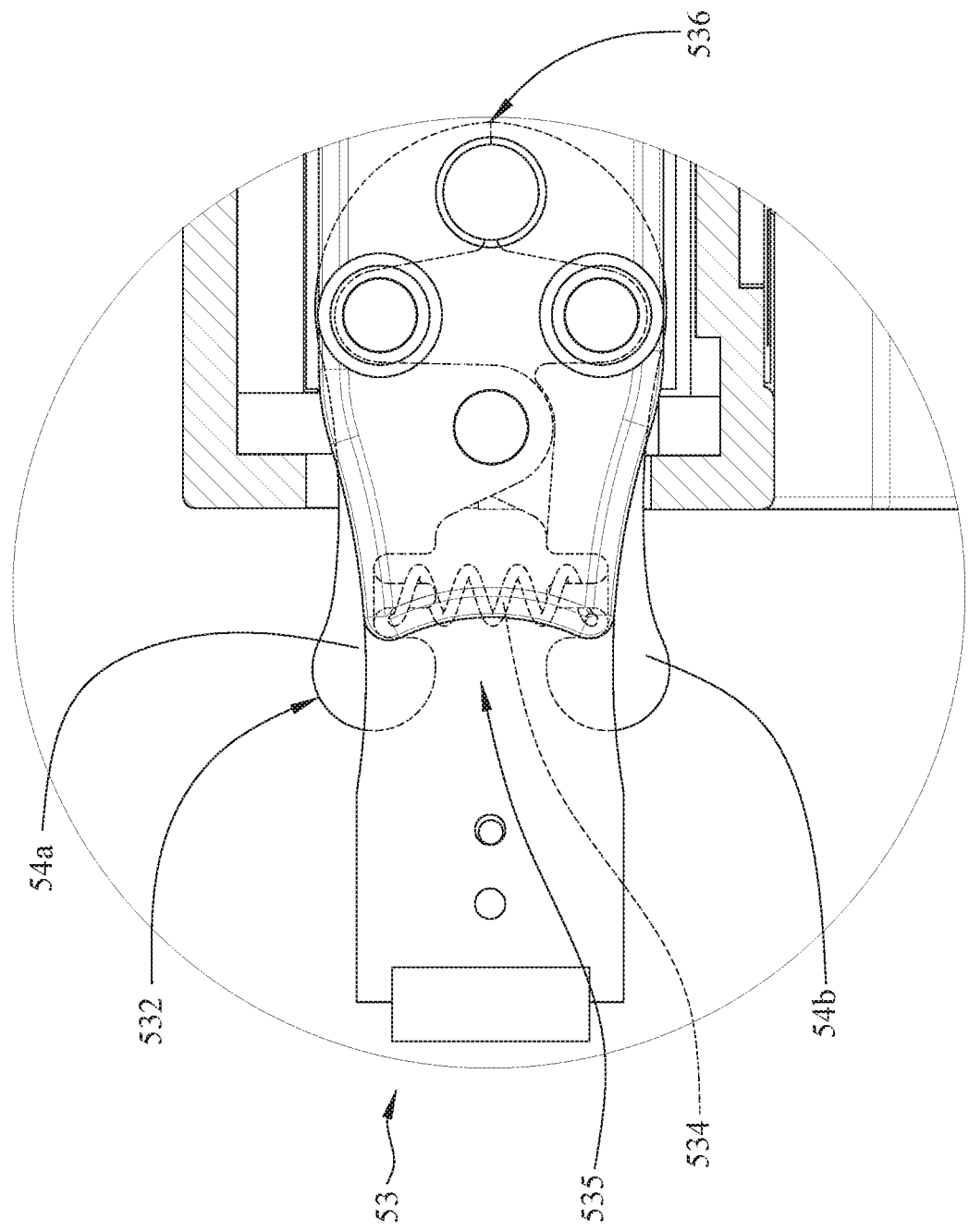
FIG. 14 is a top view of the propelling block of the smart drug injection device of the preferred embodiment of the present invention.

FIG. 14 is a top view of the propelling block 53 of the smart drug injection device of the preferred embodiment of the present invention. As shown in FIG. 14, when assembling the syringe 40, as the amount of drug in the syringe 40 is different, the position of the bottom end of the needle holder 42 will also be different. Therefore, in the preferred embodiment of the present invention, the propelling block 53 further comprises a positioning clamp 532, the positioning clamp 532 comprises two clamp bodies 54a, 54b and an elastic element 534, the two clamp bodies 54a, 54b are pivotally connected to each other, and the two ends of the clamp bodies 54a, 54b respectively have a first clamping opening 535 and a second clamping opening 536, the elastic element 534 is disposed on the first clamping opening 535, two ends of the elastic element 534 are respectively connected with the clamping bodies 54a, 54b, and the second clamping opening 536 is clamped on the screw rod 52.

Figure 15:
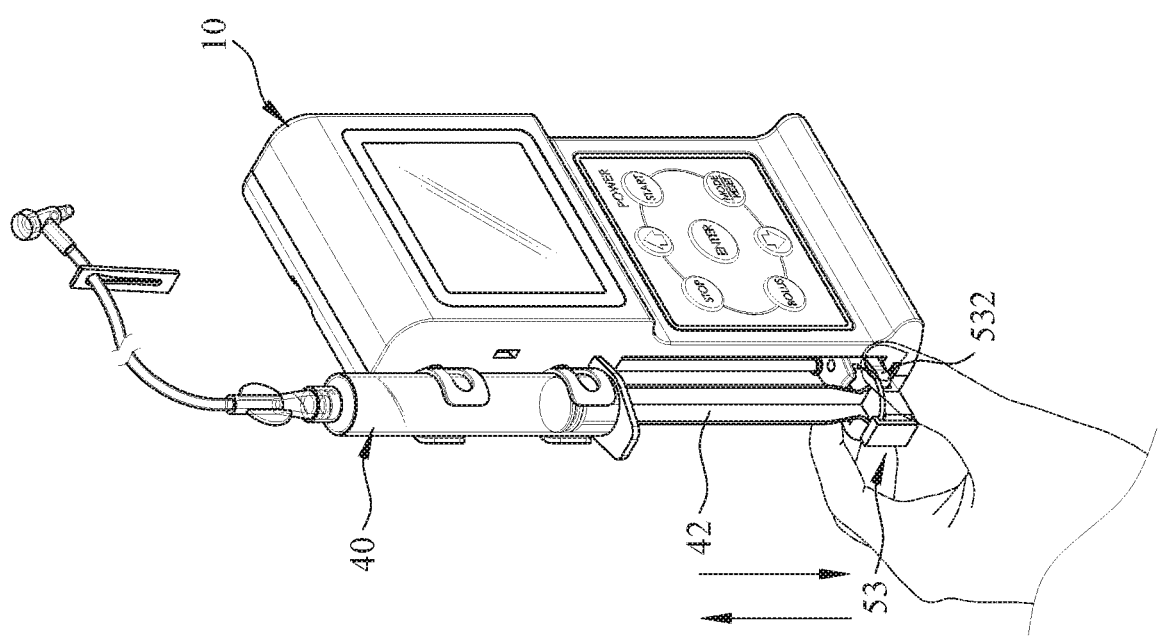
FIG. 15 is a schematic view of manually pushing the propelling block of the smart drug injection device of the preferred embodiment of the present invention.

FIG. 15 is a schematic view of manually pushing the propelling block 53 of the smart drug injection device of the preferred embodiment of the present invention. As shown in FIG. 15, when assembling the syringe 40, the user can press one end of the two clamp bodies 54a, 54b of the positioning clamp 532 simultaneously. The first clamping opening 535 is shrunk, and the second clamping opening 536 becomes larger, so that the screw rod 52 is disengaged from the second clamping opening 536 of the two clamping bodies 54a, 54b. At this point, the propelling block 53 can move freely along the screw rod 52, as shown in the arrow direction of FIG. 15, the user can manually move the propelling block 53 to achieve manually adjusting the position of the propelling block 53.

As shown in FIG. 2, in the preferred embodiment of the present invention, the main body 10 further includes a battery 92, a battery holder 90 and a battery cover 91; the battery 92 is electrically connected to the control unit 21. When the power button 12 is pressed, the control unit 21 controls the battery 92 to be on or off. The battery 92 is detachably disposed in the battery holder 90, and the battery cover 91 is disposed on the battery holder 90.

After the battery 92 is installed in the battery holder 90, the smart drug injection device will start, and the display 30 will display a welcome screen and a remaining power capacity. After 10 seconds of standby, the display 30 will be turned off and enter a black screen power saving-state state. When using the smart drug injection device, the user can press any button to start the standby screen.

The effect of the present invention is that after the user inputs the patient information to the storage unit 22, the control unit 21 controls the transmission mechanism 50 so that the syringe 40 can perform injection automatically, and the understaff problem in the hospital is improved, and the nursing staff does not need to stand by the patient all the time, as well as to prevent the nursing staff from accidentally forgetting the injection due to busyness and delaying the patient's treatment. At the same time, the treatment and results are recorded so as to provide medical staff for reference and observation.

Furthermore, the timing unit 32 and the control unit 21 enable the syringe 40 to automatically perform microinjections at regular intervals, avoiding the situation where the dosage of the drug is not accurate, and avoiding excessive dosage by hospitals and clinics to save time, leading to poor result of treatment.

In addition, the present invention is simple in structure, small in size and convenient to carry, which eliminates the need for patients to wait in the hospital for a long time.

Wherein, the control unit 21 of the present invention follow a plan for the patient made by the physician, then store the treatment course, result, time and personal data in the storage unit 22, and display the corresponding information status, pattern and provision of light source at night under the setting through the display 30, which is convenient for medical staff to observe; wherein, the information and patterns can be battery capacity, physiological model calculation of injection dosage and concentration, injection in progress, total dosage and warnings.

Although the present invention has been described with reference to the preferred embodiments thereof, it is apparent to those skilled in the art that a variety of modifications and changes may be made without departing from the scope of the present invention which is intended to be defined by the appended claims.

What is claimed is:
1. A smart drug injection device, comprising:
a main body, comprising an accommodating space and a power button, and the power button being disposed on a surface of the main body;
a circuit board, disposed in the accommodating space and comprising a control unit and a storage unit, the control unit being electrically connected to the storage unit and the power button, and the storage unit being used to store a weight value;

a display, disposed on the surface of the main body and electrically connected to the control unit, and used to display the weight value;

a syringe, disposed on one side of the main body and comprising a cylinder and a needle holder, the cylinder being used to contain a drug, one end of the cylinder being disposed the main body, and the propelling block is protrudingly disposed on the same side of the main body where the positioning sleeve is disposed, and the positioning sleeve is used for fastening the cylinder.

2. The smart drug injection device according to claim 1, wherein the main body further comprises an up button, a down button, a confirm button, and a stop button; the up button, the down button, the confirm button and the stop button are arranged on the surface of the main body and are electrically connected to the control unit; when the up button is pressed, the weight value in the storage unit is increased; when the down button is pressed, the weight value in the storage unit is decreased; when the confirm button is pressed, the storage unit sends the weight value to the control unit; when the stop button is pressed, the control unit stops the motor operation.

3. The smart drug injection device according to claim 2, wherein the circuit board further comprises a timing unit, electrically connected to the control unit; when the confirm button is pressed, the timing unit starts to count down from a predetermined time value, and sends a time message to the control unit for every interval of time, so that the control unit controls the motor to drive the screw rod to rotate to move the propelling block; when the countdown is completed, an alarm is issued to remind the medical staff; wherein the display is used to display the predetermined time value.

4. The smart drug injection device according to claim 1, wherein the smart drug injection device further comprises at least one positioning sleeve, which is disposed on one side of the main body, and the propelling block is protrudingly disposed on the same side of the main body where the positioning sleeve is disposed, and the positioning sleeve is used for fastening the cylinder.

5. The smart drug injection device according to claim 4, wherein the main body further comprises a positioning hole opened on one side of the main body and located between the positioning sleeve and the propelling block, and the cylinder comprises a wing portion inserted into the positioning hole.

6. The smart drug injection device according to claim 1, wherein the smart drug injection device further comprises a protective cover, the protective cover has a hole, the hole is opened at one end of the protective cover, the protective cover is detachably disposed on one side of the main body, the syringe is disposed inside the protective cover, and the hole is used for the cylinder to pass through.

7. The smart drug injection device according to claim 1, wherein the propelling block further comprises at least two latch holes, the moveable clamp further comprises a latch block and an elastic piece, the latch block is disposed on the elastic piece, and the latch block can be selectively disposed in one of the at least two latch holes.

8. The smart drug injection device according to claim 1, wherein the syringe further comprises a delivery tube and a sheath clamp, one end of the delivery tube is connected to the needle, the sheath clamp comprises a channel, the channel has a large-diameter end and a small-diameter end, an inner diameter of the large-diameter end is greater than an outer diameter of the delivery tube, an inner diameter of the small-diameter end is smaller than the outer diameter of the delivery tube, and the delivery tube is movably disposed in the channel.

* * * * *